United States Patent
Candau

(10) Patent No.: US 7,316,808 B2
(45) Date of Patent: Jan. 8, 2008

(54) PHASE INVERTED OIL-IN-WATER PHOTOPROTECTIVE EMULSIONS COMPRISING NANOPIGMENTS OF METAL OXIDES AND 4,4-DIARYLBUTADIENE UV-A SUNSCREENS

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 798 days.

(21) Appl. No.: 10/823,640

(22) Filed: Apr. 14, 2004

(65) Prior Publication Data

US 2004/0228813 A1 Nov. 18, 2004

Related U.S. Application Data

(60) Provisional application No. 60/468,059, filed on May 6, 2003.

(30) Foreign Application Priority Data

Apr. 14, 2003 (FR) .................... 03 04645

(51) Int. Cl.
*A61Q 17/04* (2006.01)
*A61Q 19/00* (2006.01)
*A61K 8/00* (2006.01)
*A61K 8/04* (2006.01)
*A61K 8/06* (2006.01)

(52) U.S. Cl. .......... 424/59; 424/60; 424/400; 424/401

(58) Field of Classification Search ......... 424/59, 424/60, 400, 401
See application file for complete search history.

(56) References Cited

U.S. PATENT DOCUMENTS

| 5,670,139 | A | 9/1997 | Allard et al. |
| 6,191,301 | B1 | 2/2001 | Habeck et al. |
| 6,387,355 | B2 | 5/2002 | Heidenfelder et al. |
| 2002/0004034 | A1 | 1/2002 | Heidenfelder et al. |

FOREIGN PATENT DOCUMENTS

| EP | 0 668 071 A1 | 8/1995 |
| EP | 0 916 335 A2 | 5/1999 |
| FR | 2 818 128 A1 | 6/2002 |
| JP | 7-252124 | 10/1995 |
| JP | 2001-261540 | 9/2001 |

OTHER PUBLICATIONS

Japanese Notice of Rejection issued in counterpart Japanese Patent Application No. 2004-119674on Aug. 2, 2005, 3 pages.
French Search Report Issued in French Priority Counterpart FR 03/04645 on Jan. 19, 2004, 2 pages.

*Primary Examiner*—Shelley A. Dodson
(74) *Attorney, Agent, or Firm*—Buchanan, Ingersoll & Rooney, PC

(57) ABSTRACT

Stable UV-photoprotective, phase inverted oil-in-water emulsions, well suited for the photoprotection of the skin, lips and/or hair, the average size of the globules which constitute the oily phase thereof ranging from 100 nm to 1,000 nm, contain inorganic metal oxide nanopigments and at least one organic UV-screening agent, and which also contain at least one organic 4,4-diarylbutadiene UV-A-screening agent.

30 Claims, No Drawings

PHASE INVERTED OIL-IN-WATER PHOTOPROTECTIVE EMULSIONS COMPRISING NANOPIGMENTS OF METAL OXIDES AND 4,4-DIARYLBUTADIENE UV-A SUNSCREENS

CROSS-REFERENCE TO PRIORITY/PROVISIONAL APPLICATIONS

This application claims priority under 35 U.S.C. § 119 of FR 03/04645, filed Apr. 14, 2003, and of provisional application Ser. No. 60/468,059, filed May 6, 2003, both hereby expressly incorporated by reference and both assigned to the assignee hereof. This application is also a continuation of said '059 provisional.

BACKGROUND OF THE INVENTION

1. Technical Field of the Invention

The present invention relates to oil-in-water emulsions in which the average size of the globules which constitute the oily phase of said emulsions ranges from 100 nm to 1,000 nm, comprising inorganic nanopigments based on metal oxides and at least one organic UV-screening agent, said at least one organic UV-screening agent comprising a 4,4-diarylbutadiene UV-A sunscreen.

This invention also relates to a method for formulating these compositions and their use in the abovementioned cosmetic application.

2. Description of Background and/or Related and/or Prior Art

It is well known that light radiation having wavelengths of between 280 nm and 400 nm allows tanning of the human epidermis, and that rays having wavelengths of between 280 nm and 320 nm, known by the name UV-B, cause erythemas and skin burns which can hamper the development of the natural tan; this UV-B radiation must therefore be screened out.

It is also known that UV-A rays having wavelengths of between 320 nm and 400 nm, which cause tanning of the skin, are capable of inducing its impairment, in particular in the case of a sensitive skin or a skin continually exposed to solar radiation. UV-A rays cause in particular a loss of elasticity of the skin and the appearance of wrinkles which lead to premature aging. They promote the onset of the erythematous reaction or amplify this reaction in some subjects and may even be responsible for phototoxic or photoallergic reactions. It is therefore desirable to also screen out UV-A radiation.

Numerous cosmetic compositions intended for photoprotecting the skin have been proposed to date and the use of nanopigments of metal oxides such as nanopigments of TiO2 in antisun/sunscreen products is increasingly frequent because they make it possible to obtain very high protection indices in combination with conventional UV-screening agents.

Oil-in-water emulsions are in general more highly appreciated by the consumer than water-in-oil emulsions in particular because of their pleasant feel and their presentation in the form of a non-greasy cream or milk.

One of the major disadvantages of the O/W type antisun compositions known to date and more particularly of those containing nanopigments of metal oxide, in particular of titanium, is that once applied to the skin in the form of a film, they produce thereon a lightening effect which is cosmetically undesirable and generally little appreciated by the users. This effect is all the more marked if the concentration of nanopigments in the emulsion is high and if the distribution, after application, on the skin is uneven and non-homogeneous. This poor distribution of the nanopigments which is observed at the surface of the skin is often linked to the fact that there is a substantial lack of homogeneity (poor dispersion of the pigment in its carrier) in the actual initial emulsion (before application).

To remedy this problem, specific O/W emulsions obtained according to the so-called "phase inversion" technique (PIT) have been proposed.

In order to be able to obtain good protection both in the range of UV-A rays and in the UV-B range, organic screening agents which are active in UV-A, combined with organic screening agents which are active in UV-B, are most often used in this type of composition.

Among the available organic UV-A-screening agents, a family of compounds which is particularly effective in UV-A is 1,4-benzene[di(3-methylidene-10-camphorsulphonic)] acid and its different salts, which is described in particular in FR-A-2,528,420 and FR-A-2,639,347; they are indeed capable of absorbing ultraviolet rays having wavelengths of between 280 nm and 400 nm, with absorption maxima of between 320 nm and 400 nm, in particular in the region of 345 nm.

However, the specific O/W emulsions obtained according to the so-called "phase inversion" technique containing nanopigments and UV-A-screening agents of this type lose their UV-protection efficacy and in particular UV-A-protection efficacy when they come into contact with water; indeed, these screening agents have a tendency to disappear with water, with bathing in the sea or in a swimming pool, under the shower or during the practice of water sports; thus, these antisun/sunscreen compositions no longer provide the desired initial protection when the substrate (skin or hair) to which they have been applied comes into contact with water.

Thus, the need still remains for providing antisun/sunscreen compositions of the O/W emulsion type obtained according to the so-called "phase inversion" technique based on nanopigments of metal oxides and at least one organic UV-A-screening agent of comparable efficacy to that of 1,4-benzene[di(3-methylidene-10-camphorsulphonic)] acid and its different salts which are stable over time and are resistant to water (stability to water) and whose cosmetic performance would be comparable to that obtained with conventional oil/water emulsions.

SUMMARY OF THE INVENTION

It has now unexpectedly and surprisingly been determined that it is possible to ameliorate or overcome the various disadvantages indicated above by providing a UV-A-screening agent of the 4,4-diarylbutadiene type in a carrier of the O/W emulsion type obtained according to the so-called "phase inversion" technique based on nanopigments of metal oxide.

This discovery forms the basis of the present invention.

Thus, the present invention features oil-in-water emulsions obtained via the phase inversion technique, in which the average size of the globules which constitute the oily phase of said emulsions ranges from 100 nm to 1,000 nm and comprising inorganic nanopigments based on metal oxides and at least one organic UV-screening agent, said at least one organic UV-A-screening agent being of 4,4-diarylbutadiene type.

Other characteristics, aspects and advantages of the invention will be seen from the detailed description which follows.

DETAILED DESCRIPTION OF BEST MODE AND SPECIFIC/PREFERRED EMBODIMENTS OF THE INVENTION

The compositions in accordance with the invention contain at least one nanopigment of a metal oxide selected from among those of titanium, cerium, zirconium, zinc and iron oxides, or mixtures thereof.

The expression nanopigment is understood to mean a pigment whose average elementary particle size is greater than 5 nm and less than 100 nm. According to a preferred embodiment of the invention, this size preferably ranges from 10 nm to 50 nm.

The nanopigments may be coated or uncoated.

The coated pigments are pigments which have undergone one or more surface treatments of a chemical, electronic, mechanochemical and/or mechanical nature with compounds, as described for example in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin) alkanolamines, silicon oxides, metal oxides or sodium hexametaphosphate.

In a known manner, the silicones are organosilicon polymers or oligomers with a linear or cyclic, branched or crosslinked structure, having a variable molecular weight, which are obtained by polymerization and/or polycondensation of suitably functionalized silanes, and mainly comprising a repetition of principal units in which the silicon atoms are linked to each other by oxygen atoms (siloxane bond), optionally substituted hydrocarbon radicals being directly linked via a carbon atom to the said silicon atoms.

The term "silicones" also encompasses the silanes necessary for their preparation, in particular alkylsilanes.

The silicones used for coating the nanopigments suitable for the present invention are preferably selected from the group consisting of alkylsilanes, polydialkylsiloxanes and polyalkylhydrogenosiloxanes. More preferably still, the silicones are selected from the group consisting of octyltrimethylsilane, polydimethylsiloxanes and polymethylhydrogenosiloxanes.

Of course, the nanopigments of metal oxides, before their treatment with silicones, may have been treated with other surface-active agents, in particular with cerium oxide, alumina, silica, aluminum compounds, silicon compounds, or mixtures thereof.

The coated pigments are more particularly titanium oxides coated:

with silica, such as the product "SUNVEIL" from IKEDA;

with silica and iron oxide, such as the product "SUNVEIL F" from IKEDA;

with silica and alumina, such as the products "MICROTITANIUM DIOXIDE MT 500 SA" and "MICROTITANIUM DIOXIDE MT 100 SA" from TAYCA, "TIOVEIL" from TIOXIDE;

with alumina, such as the products "TIPAQUE TTO-55 (B)" and "TIPAQUE TTO-55 (A)" from ISHIHARA, and "UVT 14/4" from KEMIRA;

with alumina and aluminum stearate, such as the product "MICROTITANIUM DIOXIDE MT 100 T, MT 100 TX, MT 100 Z" from TAYCA;

with alumina and aluminum laurate, such as the product "MICROTITANIUM DIOXIDE MT 100 S" from TAYCA;

with iron oxide and iron stearate, such as the product "MICROTITANIUM DIOXIDE MT 100 F" from TAYCA;

with zinc oxide and zinc stearate, such as the product "BR 351" from TAYCA;

with silica and alumina and treated with a silicone, such as the products "MICROTITANIUM DIOXIDE MT 600 SAS", "MICROTITANIUM DIOXIDE MT 500 SAS" or "MICROTITANIUM DIOXIDE MT 100 SAS" from TAYCA;

with silica, alumina, aluminum stearate and treated with a silicone, such as the product "STT-30-DS" from TITAN KOGYO;

with alumina and treated with a silicone, such as the products "TIPAQUE TTO-55 (S)" from ISHIHARA, or "UV TITAN M 262" from KEMIRA;

with triethanolamine, such as the product "STT-65-S" from TITAN KOGYO;

with stearic acid, such as the product "TIPAQUE TTO-55 (C)" from ISHIHARA;

with sodium hexametaphosphate, such as the product "MICROTITANIUM DIOXIDE MT 150 W" from TAYCA.

Other titanium oxide nanopigments treated with a silicone are preferably TiO2 treated with octyltrimethylsilane and whose average elementary particle size ranges from 25 nm to 40 nm, such as that sold under the trademark "T 805" by DEGUSSA SILICES, $TiO_2$ treated with a polydimethylsiloxane and whose average elementary particle size is 21 nm, such as that sold under the trademark "70250 CARDRE UF TiO2S13" by CARDRE, TiO2 anatase/rutile treated with a polydimethylhydrogenosiloxane and whose average elementary particle size is 25 nm, such as that sold under the trademark "MICRO TITANIUM DIOXYDE USP GRADE HYDROPHOBIC" by COLOR TECHNIQUES.

The uncoated titanium oxide nanopigments are for example sold by TAYCA under the trademarks "MICROTITANIUM DIOXIDE MT 500 B" or "MICROTITANIUM DIOXIDE MT600 B" by DEGUSSA under the name "P 25", by WACKHER under the name "transparent titanium oxide PW", by MIYOSHI KASEI under the name "UFTR", by TOMEN under the name "ITS" and by TIOXIDE under the name "TIOVEIL AQ".

The uncoated zinc oxide nanopigments are, for example:

those marketed under the name "Z-COTE" by SUNSMART;

those marketed under the name "NANOX" by ELEMENTIS;

those marketed under the name "NANOGARD WCD 2025" by NANOPHASE TECHNOLOGIES.

The coated zinc oxide nanopigments are, for example:

those marketed under the name "OXIDE ZINC CS-5" by Toshibi (ZnO coated with polymethylhydrogenosiloxane);

those marketed under the name "NANOGARD ZINC OXIDE FN" by NANOPHASE TECHNOLOGIES (as a 40% dispersion in Finsolv TN, $C_{12}$-$C_{15}$ alcohol benzoate);

those marketed under the name "DAITOPERSION ZN-30" and "DAITOPERSION ZN-50" by Daito (dispersions in oxyethylenated cyclopolymethylsiloxane/polydimethylsiloxane, containing 30% or 50% of zinc nanooxides coated with silica and polymethylhydrogenosiloxane);

those marketed under the name "NFD ULTRAFINE ZNO" by Daikin (ZnO coated with perfluoroalkyl phosphate and copolymer based on perfluoroalkylethyl in dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "ESCALOL Z100" by ISP (ZnO treated with alumina and dispersed in the ethylhexyl methoxycinnamate/PVP-hexadecene copolymer/methicone mixture);

those marketed under the name "FUJI ZNO-SMS-10" by Fuji Pigment (ZnO coated with silica and polymethylsilsesquioxane);

those marketed under the name "NANOX GEL TN" by Elementis (ZnO dispersed at 55% in $C_{12}$-$C_{15}$ alcohol benzoate with polycondensate of hydroxystearic acid).

The uncoated cerium oxide nanopigments are sold under the name "COLLOIDAL CERIUM OXIDE" by RHONE POULENC.

The uncoated iron oxide nanopigments are, for example, sold by ARNAUD under the names "NANOGARD WCD 2002 (FE 45B)", "NANOGARD IRON FE 45 BL AQ", "NANOGARD FE 45R AQ", "NANOGARD WCD 2006 (FE 45R)" or by MITSUBISHI under the name "TY-220".

The coated iron oxide nanopigments are, for example, sold by ARNAUD under the names "NANOGARD WCD 2008 (FE 45B FN)", "NANOGARD WCD 2009 (FE 45B 556)", "NANOGARD FE 45 BL 345", "NANOGARD FE 45 BL", or by BASF under the name "OXYDE DE FER TRANSPARENT".

There may also be mentioned mixtures of metal oxides, in particular of titanium dioxide and of cerium dioxide, including the equiponderous mixture of titanium dioxide and of cerium dioxide coated with silica, sold by IKEDA under the name "SUNVEIL A" and the mixture of titanium dioxide and zinc dioxide coated with alumina, silica and silicone, such as the product "M 261" sold by KEMIRA or coated with alumina, silica and glycerine such as the product "M 211" sold by KEMIRA.

According to the invention, the coated or uncoated titanium oxide nanopigments are particularly preferred.

The titanium oxide may be provided in rutile, anatase or amorphous form, but preferably in rutile and/or anatase form and/or in amorphous or substantially amorphous form.

Depending on their more or less pronounced lipophilic, or on the contrary hydrophilic, character, the nanopigments may be present either in the fatty phase of the emulsion, or in the aqueous phase, or even in both phases at the same time.

The nanopigments in accordance with the invention represent in general from 0.5% to 40%, preferably from 1% to 30%, of the total weight of the emulsion.

The 4,4-diarylbutadiene compounds in accordance with the invention are preferably selected from among those corresponding to the following formula (I):

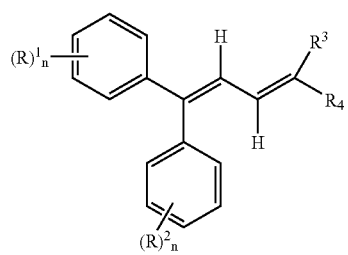

(I)

in which the diene system is of the Z,Z; Z,E; E,Z or E,E configuration or mixtures of the said configurations, and wherein:

$R^1$ and $R^2$, which may be identical or different, are each hydrogen, a $C_1$-$C_{20}$ alkyl radical, a $C_2$-$C_{10}$ alkenyl radical, a $C_1$-$C_{12}$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulphonate residue or an ammonium residue;

$R^3$ is a group $COOR^5$, $COR^5$, $CONR^5R^6$, CN, O=S(—$R^5$)=O, O=S(—$OR^5$)=O, $R^7$O—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

$R^4$ is a group $COOR^6$, $COR^6$, $CONR^5R^6$, CN, O=S(—$R^6$)=O, O=S(—$OR^6$)=O, $R^7$O—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

the radicals $R^5$ to $R^8$, which may be identical or different, are each hydrogen, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ bicycloalkenyl radical, a $C_7$-$C_{10}$ cycloalkenyl radical, an optionally substituted aryl radical, an optionally substituted heteroaryl radical;

n ranges from 1 to 3; with the proviso that the radicals $R^3$ to $R^8$ can together form, with the carbon atoms from which they depend, a $C_5$-$C_6$ ring which may be fused.

As $C_1$-$C_{20}$ alkyl radicals, there may be mentioned, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

As $C_2$-$C_{10}$ alkenyl groups, there may be mentioned, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl, n-decenyl.

As $C_1$-$C_{12}$ alkoxy radicals, there may be mentioned: methoxy, n-propxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

As $C_1$-$C_{20}$ alkoxycarbonyl radicals, there may be mentioned esters of $C_1$-$C_{20}$ alcohols.

As $C_1$-$C_{12}$ monoalkylamino or dialkylamino radicals, there may be mentioned those in which the alkyl radical(s) is(are) selected from among methyl, n-propyl, 2-methylpropyl, 1,1-dimethylethyl, hexyl, heptyl, 2-ethylhexyl, isopropyl, 1-methylpropyl, n-pentyl, 3-methylbutyl, 2,2-dimethylpropyl, 1-methyl-1-ethylpropyl, octyl.

As $C_3$-$C_{10}$ cycloalkyl radicals, there may be mentioned, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$-$C_{10}$ cycloalkenyl radicals having one or more double bonds, there may be mentioned: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctetraenyl, cyclononenyl or cyclodecenyl.

The cycloalkyl or cycloalkenyl radicals may comprise one or more substituents (preferably from 1 to 3) selected, for example, from among halogens such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl; they may also comprise from 1 to 3 heteroatoms such as sulphur, oxygen or nitrogen whose free valencies may be saturated with a hydrogen or a $C_1$-$C_4$ alkyl radical.

The bicycloalkyl or bicycloalkenyl groups are selected, for example, from among bicyclic terpenes such as pinane, bornane, pinene or camphor or adamantane derivatives.

The aryl groups are preferably selected from phenyl or naphthyl rings, which may comprise one or more substituents (preferably from 1 to 3) selected for example from halogen such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl. Phenyl, methoxyphenyl, naphthyl and thienyl are more particularly preferred.

The heteroaryl groups comprise in general one or more heteroatoms selected from among sulphur, oxygen or nitrogen.

The water-solubilizing groups are, for example, carboxyl and sulphoxy residues, and more particular their salts with physiologically acceptable cations such as alkali metal salts or trialkylammonium salts such as tri(hydroxyalkyl)ammonium or 2-methylpropan-1-ol-2-ammonium salts. There may also be mentioned ammonium groups such as alkylammoniums and their salified forms with physiologically acceptable anions.

The compounds of formula (I) are known per se and their structures and their syntheses are described in DE-1,9,755,649, EP-916,335, EP-1,133,980 and EP-1,133,981.

By way of example of a compound of formula (I), the following compounds are representative:

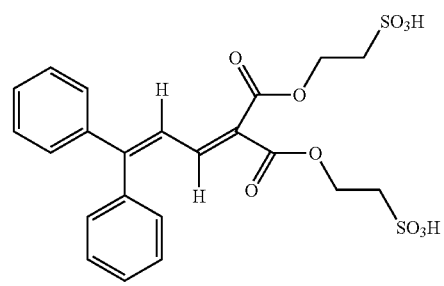
(compound a)

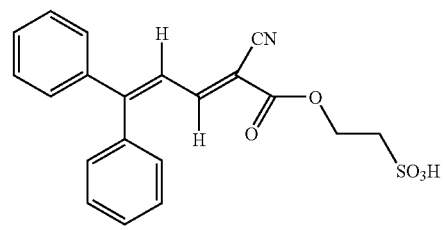
(compound b)

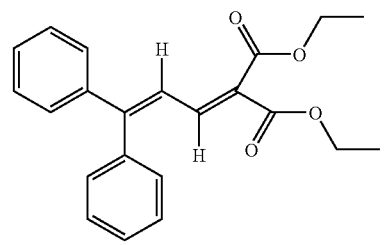
(compound c)

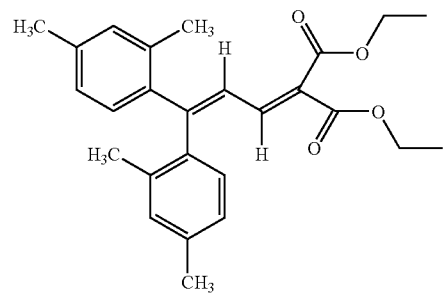
(compound d)

-continued (compound e)

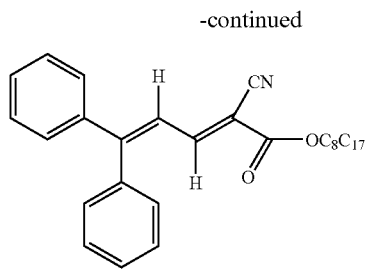

(compound f)

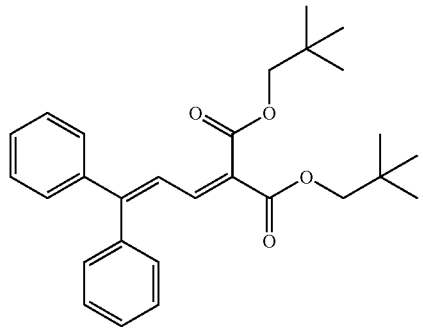

The preferred compounds of formula (I) are those in which: n=1 or 2;

$R^1$ and $R^2$, which may be identical or different, are each hydrogen, a $C_1$-$C_{20}$ alkyl radical, a $C_1$-$C_{12}$ alkoxy radical, a $C_1$-$C_{12}$ monoalkylamino radical, a $C_1$-$C_{12}$ dialkylamino radical, a water-solubilizing substituent selected from among a carboxylate group, a sulphonate group or an ammonium residue;

$R^3$ is a group $COOR^5$, $COR^5$, $CONR^5R^6$, a $C_1$-$C_{20}$ alkyl radical, a $C_3$-$C_{10}$ cycloal radical, a $C_3$-$C_{10}$ cycloalkenyl radical, a $C_7$-$C_{10}$ bicycloalkyl radical, optionally substituted phenyl, naphthyl or thienyl;

$R^4$ is a group $COOR^6$, $COR^6$, $CONR^5R^6$, a $C_1$-$C_{20}$ alkyl radical, a $C_3$-$C_6$ cycloalk radical, a $C_3$-$C_{10}$ cycloalkenyl radical, a $C_7$-$C_{10}$ bicycloalkyl radical, optionally substituted phenyl, naphthyl or thienyl;

the radicals $R^5$ and $R^6$, which may be identical or different, are each hydrogen, a $C_1$-$C_{12}$ alkyl radical, a $C_3$-$C_{10}$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

Among these compounds, there are more particularly preferred those in which:

$R^1$ and $R^2$, which may be identical or different, are each hydrogen, a $C_1$-$C_{20}$ alkyl radical, a $C_1$-$C_{20}$ alkoxy radical, a water-solubilizing substituent selected from among a carboxylate group, a sulphonate group or an ammonium residue;

$R^3$ is a group $COOR^5$, $COR^5$, $CONR^5R^6$;

$R^4$ is a group $COOR^6$, $COR^6$, $CONR^5R^6$;

the radicals $R^5$ and $R^6$, which may be identical or different, are each hydrogen, a $C_1$-$C_{12}$ alkyl radical, a $C_3$-$C_6$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

According to a particularly preferred embodiment, the compounds of formula (I) are selected from among those of the following formula (I'):

(I')

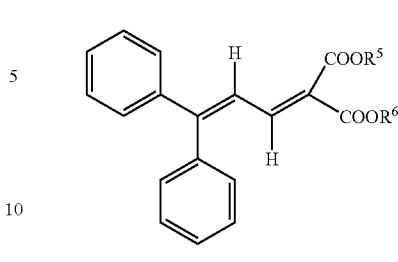

wherein the radicals $R^5$ and $R^6$, which may be identical or different, are each hydrogen, a $C_1$-$C_{20}$ alkyl radical, a $C_3$-$C_6$ cycloalkyl radical, a $C_3$-$C_{10}$ cycloalkenyl radical.

Among these compounds of formula (I'), there may be mentioned, more particularly, 1,1-dicarboxy(2,2'-dimethylpropyl)-4,4-diphenylbutadiene having the structure:

(compound f)

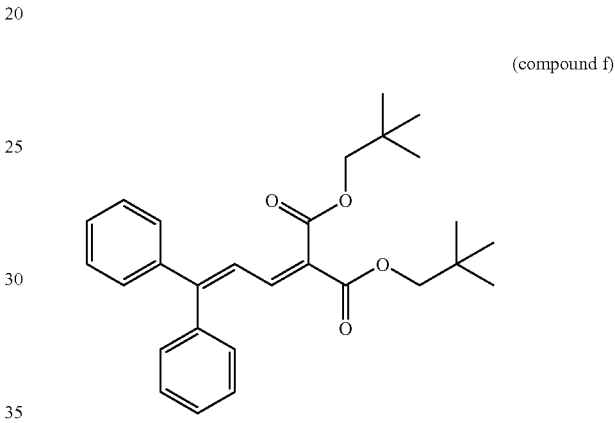

Another 4,4-diarylbutadiene family which may be formulated into the emulsions according to the invention are those corresponding to the following formula (II):

(II)

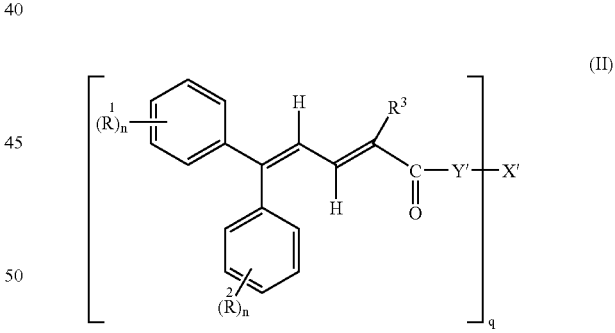

in which the diene system is of the Z,Z; Z,E; E,Z or E,E configuration or mixtures of the said configurations and wherein:

$R^1$, $R^2$, $R^3$ and n have the same meanings indicated in the preceding formula (I);

Y' is a group —O— or —$NR^9$—;

$R^9$ is hydrogen, a linear or branched $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an aryl radical, a heteroaryl radical;

X' is a residue of a linear or branched, aliphatic or cycloaliphatic $C_2$-$C_{20}$ polyol comprising from 2 to 10 hydroxyl groups and having the valency q; with the proviso that the carbon chain of the said residue may be interrupted by one or more sulphur or oxygen atoms, one or more imine groups, one or more $C_1$-$C_4$ alkylimino groups;

q ranges from 2 to 10; and

X' is a polyol $C_2$-$C_{20}$ residue containing from 2 to 10 hydroxyl groups, and in particular:

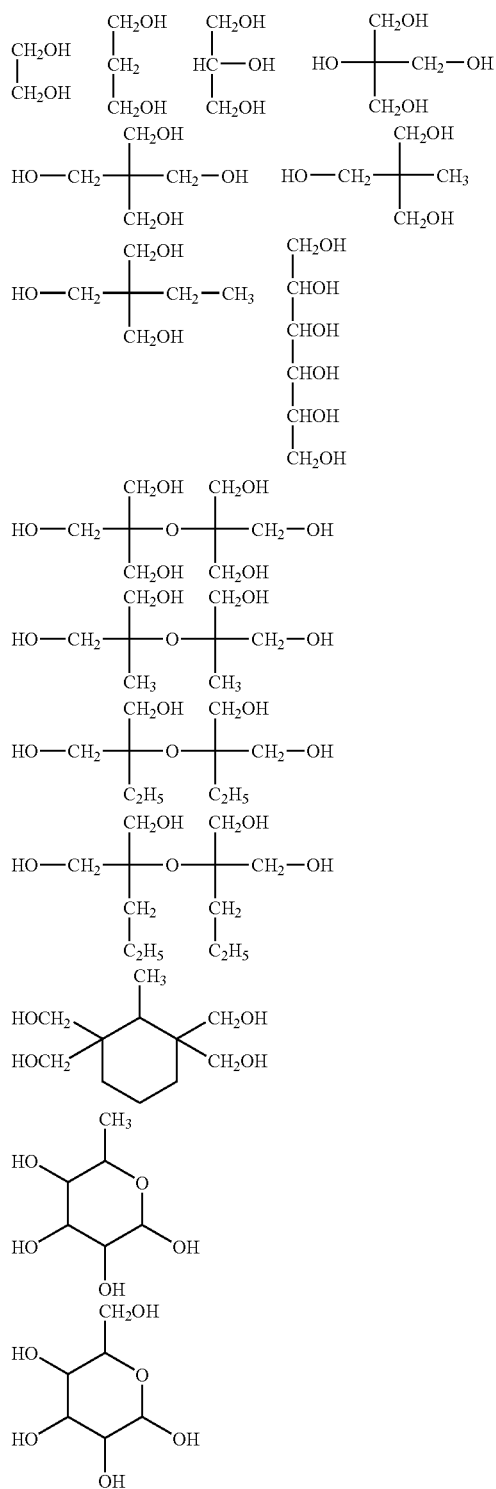

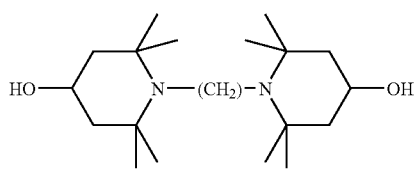

The more preferred compounds of formula (II) are those in which:

$R^1$ and $R^2$, which may be identical or different, are each hydrogen, a $C_1$-$C_{12}$ alkyl radical, a $C_1$-$C_8$ alkoxy radical, a water-solubilizing substituent selected from among a carboxylate group, a sulphonate group or an ammonium residue;

$R^3$ is a group $COOR^5$, $CONR^5R^6$, CN, a $C_3$-$C_{10}$ cycloalkyl radical, a $C_7$-$C_{10}$ bicycloalkyl radical;

$R^5$ and $R^6$, which may be identical or different, are each a linear or branched $C_1$-$C_{20}$ alkyl radical, a $C_3$-$C_{10}$ cycloalkyl radical, a $C_7$-$C_{10}$ bicycloalkyl radical, optionally substituted naphthyl or phenyl;

X' is a polyol residue comprising from 2 to 6 hydroxyl groups and more particularly from 2 to 4.

The still more preferred compounds of formula (II) are those in which: X' is an ethanol or pentaerythritol residue.

The even more particularly preferred compounds of formula (II) are selected from among:

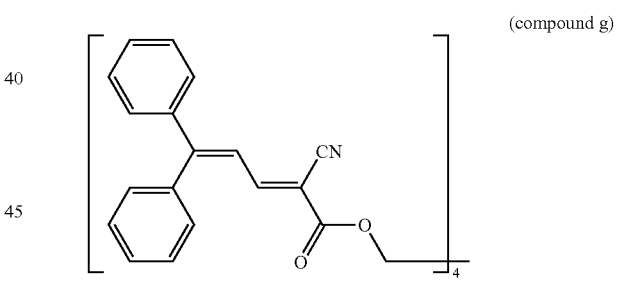

(compound g)

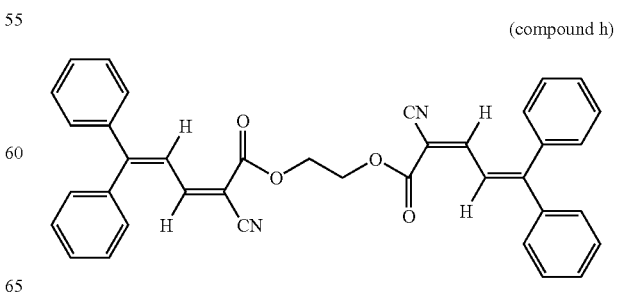

(compound h)

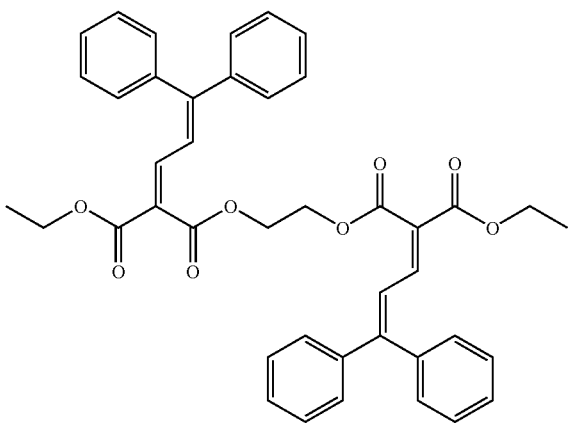
(compound i)

The compounds of formula (II) as defined above are known per se and their structures and their syntheses are described in EP-A-1,008,586.

The 4,4-diarylbutadiene compounds are preferably present in the compositions in proportions ranging from 0.1% to 20% by weight, more preferably from 1% to 10% by weight relative to the total weight of the composition.

The nature of the fatty phase entering into the composition of the emulsions according to the invention is not critical and it may thus comprise all the compounds which are already known in general as being suitable for the manufacture of oil-in-water type emulsions. In particular, these compounds may be selected, alone or as mixtures, from among various fatty substances, oils of plant, animal or mineral origin, natural or synthetic waxes, and the like.

Among the oils which may be formulated into the composition of the fatty phase, there may be mentioned, in particular:

mineral oils such as paraffin oil and liquid paraffin;

oils of animal origin, such as perhydrosqualene;

oils of plant origin, such as sweet almond oil, avocado oil, castor oil, olive oil, jojoba oil, sesame oil, groundnut oil, grape seed oil, rapeseed oil, copra oil, hazelnut oil, shea butter, palm oil, apricot kernel oil, calophyllum oil, rice bran oil, maize germ oil, wheat germ oil, soya bean oil, sunflower oil, evening primrose oil, safflower oil, passion flower oil and rye oil; and synthetic oils, such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate, isoparaffins and poly-□-olefins.

As other oils which can be formulated into the emulsions according to the invention, there may also be mentioned C12-C15 fatty alcohol benzoates (Finsolv TN from FINE-TEX), fatty alcohols such as lauryl, cetyl, myristyl, stearyl, palmityl or oleyl alcohol and 2-octyldodecanol, acetylglycerides, octanoates and decanoates of alcohols and polyalcohols such as those of glycol and of glycerol, ricinoleates of alcohols and polyalcohols such as those of cetyl, fatty acid triglycerides such as caprylic/capric triglycerides, C10-C18 saturated fatty acid triglycerides, fluorinated and perfluorinated oils, lanolin, hydrogenated lanolin, acetylated lanolin and finally volatile or nonvolatile silicone oils.

Of course, the fatty phase may also contain one or more conventional lipophilic cosmetic adjuvants, in particular those which are already customarily used in the manufacture and production of anti-sun cosmetic compositions.

According to one of the main characteristics of the present invention, the average size of the liquid particles (or globules) of fatty phase within the dispersive aqueous phase should be within quite specific limits, namely between 100 nm and 1,000 nm. Preferably, this average size is between 100 nm and 500 nm. More preferably still, the size distribution of the oily globules is such that most of the said globules (i.e., at least 90% in numerical terms) have a size between the limits indicated above.

Conventionally, the dispersive aqueous phase may comprise water, or a mixture of water and polyhydric alcohol(s) such as, for example, glycerol, propylene glycol and sorbitol, or alternatively a mixture of water and water-soluble lower alcohol(s) such as ethanol, isopropanol or butanol (aqueous-alcoholic solution), and it may of course additionally contain conventional water-soluble cosmetic adjuvants.

The emulsions in accordance with the invention additionally generally contain particular surfactants or emulsifiers whose use was made necessary for the preparation and production of the ultrafine emulsion. This point will be detailed below. They may additionally contain specific coemulsifiers whose role is, during the preparation of the emulsion, to substantially reduce the quantity of surfactants necessary for producing the emulsion.

As a guide, the antisun/sunscreen formulations in accordance with the invention generally have the following compositions:

(i) aqueous phase: from 50% to 95% by weight, preferably from 70% to 90% by weight, relative to the whole formulation, (ii) oily phase: from 5% to 50% by weight, preferably from 10% to 30% by weight, relative to the whole formulation, (iii) (co)emulsifier(s): from 0.5% to 20% by weight, preferably from 2% to 10% by weight, relative to the whole formulation.

The preferred method of preparing the compositions according to the invention, itself constituting another feature of the present invention, will now be developed. The method for producing these emulsions is based on the phase inversion manufacturing technique. This technique is, in its principle, well known and in particular is described in the article "Phase Inversion Emulsification", by Th Förster et al., which appeared in Cosmetics & Toiletries, vol 106, December 1991, pp 49-52. Its principle is as follows: (i) A fatty phase, on the one hand, and an aqueous phase, on the other hand, are mixed in the presence of a suitable emulsifying system and of at least one UV-A-screening agent of the 4,4-diarylbutadiene type, with stirring, the said mixing being carried out at a temperature greater than the phase inversion temperature (PIT) of the medium, so as to obtain a water-in-oil type emulsion. (ii) The temperature of the emulsion thus obtained is brought to a temperature below the said phase inversion temperature, thereby obtaining an ultrafine emulsion of the oil-in-water type. (iii) Inorganic nanopigments are introduced during the carrying out of step (i) and/or at the end of step (ii).

One of the difficulties for carrying out a method as described above lies in the suitable choice of the emulsifying system which must be appropriate for the desired result. The suitable systems are emulsifiers of the nonionic type selected from among polyoxyethylenated and/or polyoxypropylenated fatty alcohols (i.e., compounds obtained by reaction between an aliphatic fatty alcohol, such as behenyl alcohol or cetyl alcohol, with ethylene oxide or propylene oxide or an ethylene oxide/propylene oxide mixture) and esters of fatty acids and polyols, optionally polyoxyethylenated and/or polyoxypropylenated (i.e., compounds obtained by reacting a fatty acid, such as stearic acid or oleic acid, with a polyol, such as, for example, an alkylene glycol or a glycerol or a polyglycerol, optionally in the presence of ethylene oxide or propylene oxide or an ethylene oxide/propylene oxide mixture), or mixtures thereof. Moreover, and preferably, the emulsifying system selected will have an overall HLB (HLB=Hydrophilic-Lipophilic Balance, within the meaning of Griffin; see J. Soc. Cosm. Chem. 1954 (vol 5), pp 249-256; balance between the hydrophilic character and the lipophilic character of the surfactant) ranging from 9.5 to 11.5 approximately, advantageously close to 10, so as to allow the obtaining of a phase inversion at a temperature of less than 90° C. (PIT<90° C.). The content of emulsifying agent(s) is between 0.5% and 40% by weight, and preferably between 2% and 10% by weight relative to the total weight of the emulsion.

The compositions in accordance with the invention may further comprise other additional organic UV-screening agents which are active in UV-A and/or UV-B, which are water-soluble or fat-soluble or alternatively insoluble in the commonly-used cosmetic solvents. The additional organic screening agents are selected, in particular, from among the anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243 and EP-944,624; benzophenone derivatives; β,β'-diphenyl acrylate derivatives; benzotriazole derivatives; benzalmalonate derivatives; benzimidazole derivatives; imidazolines; bis-benzoazolyl derivatives as described in EP-669,323 and U.S. Pat. No. 2,463,264; p-aminobenzoic acid (PABA) derivatives; benzoxazole derivatives as described in EP-0,832,642, EP-1,027,883, EP-1,300,137 and DE-1-0,162,844; methylenebis(hydroxyphenylbenzotriazole) derivatives as described in U.S. Pat. Nos. 5,237,071, 5,166,355, GB-2,303,549, DE-1-9,726,184 and EP-893,119; screening polymers and screening silicones such as those described in particular in WO 93/04665; dimers derived from α-alkylstyrene such as those described in DE-1-9,855,649 and mixtures thereof.

As examples of organic screening agents which are active in UV-A and/or UV-B, there may be mentioned those designated below under their INCI names:

Para-Aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic Derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA Salicylate, sold under the name "NEO HELIOPAN TS" by Haarmann and REIMER,
Dibenzoylmethane Derivatives:
Butyl Methoxydibenzoylmethane sold in particular under the trademark "PARSOL 1789" by HOFFMANN LA ROCHE,
Isopropyl Dibenzoylmethane,
Cinnamic Derivatives:
Ethylhexyl Methoxycinnamate sold in particular under the trademark "PARSOL MCX" by HOFFMANN LA ROCHE,
Isopropyl Methoxy cinnamate,
Isoamyl Methoxy cinnamate sold under the trademark "NEO HELIOPAN E 1000" by HAARMANN and REIMER,
Cinoxate,
DEA Methoxycinnamate,
Diisopropyl Methylcinnamate,
Glyceryl Ethylhexanoate Dimethoxycinnamate,
β,β'-Diphenyl Acrylate Derivatives:
Octocrylene sold in particular under the trademark "UVINUL N539" by BASF,
Etocrylene, sold in particular under the trademark "UVINUL N35" by BASF,
Benzophenone Derivatives:
Benzophenone-1 sold under the trademark "UVINUL 400" by BASF,
Benzophenone-2 sold under the trademark "UVINUL D50" by BASF,
Benzophenone-3 or Oxybenzone, sold under the trademark "UVINUL M40" by BASF,
Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "UVINUL DS-49" by BASF,
Benzophenone-12,
n-Hexyl 2-(4-diethylamino-2-hydroxybenzoyl)benzoate,
Benzylidenecamphor Derivatives:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulphonic Acid manufactured under the name "MEXORYL SL" by CHIMEX,
Camphor Benzalkonium Methosulphate manufactured under the name "MEXORYL SO" by CHIMEX,
Terephthalylidene Dicamphor Sulphonic Acid manufactured under the name "MESORYL SX" by CHIMEX,
Polyacrylamidomethyl Benzylidene Camphor manufactured under the name "MESORYL SW" by CHIMEX,
Benzimidazole Derivatives:
Phenylbenzimidazole Sulphonic Acid sold in particular under the trademark "EUSOLEX 232" by MERCK,
Disodium Phenyl Dibenzimidazole Tetra-sulphonate sold under the trademark "NEO HELIOPAN AP" by Haarmann and REIMER,
Triazine Derivatives:
Anisotriazine sold under the trademark "TINOSORB S" by CIBA SPECIALTY CHEMICALS,
Ethylhexyl triazone sold in particular under the trademark "UVINUL T150" by BASF, Diethylhexyl Butamido Triazone sold under the trademark "UVASORB HEB" by SIGMA 3V,
2,4,6-Tris(diisobutyl 4'-aminobenzalmalonate)-s-triazine,
Benzotriazole Derivatives:
Drometrizole Trisiloxane sold under the name "Silatrizole" by RHODIA CHIMIE, Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS,
Anthranilic Derivatives:
Menthyl anthranilate sold under the trademark "NEO HELIOPAN MA" by Haarmann and REIMER,
Imidazoline Derivatives:
Ethylhexyl Dimethoxybenzylidene Dioxoimidazoline Propionate,
Benzalmalonate derivatives: Polyorganosiloxane with benzalmalonate functional groups such as polysilicone-15 sold under the trademark "PARSOL SLX" by HOFFMANN LAROCHE
Benzoxazole Derivatives:
2,4-Bis[5-1-(dimethylpropyl)benzoxazol-2-yl-(4-phenyl) imino]-6-(2-ethylhexyl)imino-1,3,5-triazine sold under the name Uvasorb K2A by Sigma 3V; and mixtures thereof.

The organic screening agents which are more particularly preferred are selected from among the following compounds:
Ethylhexyl Salicylate,
Ethylhexyl Methoxycinnamate,
Octocrylene,
Butyl Methoxydibenzoylmethane,
Phenylbenzimidazole Sulphonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulphonic Acid,
Disodium Phenyl Dibenzimidazole Tetra-sulphonate,
2,4,6-Tris(diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl) imino]-6-(2-ethylhexyl)imino-1,3,5-triazine and mixtures thereof.

The additional screening agents according to the invention are generally present in the compositions according to the invention in an amount ranging from 0.1% to 30% by weight, and preferably from 0.5% to 15% by weight, relative to the total weight of the composition.

The compositions according to the invention may also contain agents for artificially bronzing and/or tanning the skin (self-tanning agents).

The self-tanning agents are generally selected from mono- or polycarbonylated compounds such as for example isatin, alloxan, ninhydrin, glyceraldehyde, mesotartaric aldehyde, glutaraldehyde, erythrulose, derivatives of 4,5-pyrazolindiones as described in FR-2,466,492 and WO 97/35842, dihydroxyacetone (DHA), 4,4-dihydroxypyrazolin-5-one derivatives as described in EP-903,342. DHA will preferably be used.

DHA may be used in free form and/or encapsulated for example into lipid vesicles such as liposomes, which are described in particular in WO 97/25970.

The mono- or polycarbonylated self-tanning agents are generally present in the compositions according to the invention in proportions ranging from 0.1% to 10% by weight relative to the total weight of the composition, and preferably from 0.2% to 8% by weight relative to the total weight of the composition.

The compositions in accordance with the present invention may additionally comprise conventional cosmetic adjuvants, selected in particular from among organic solvents, ionic or nonionic thickeners, demulcents, humectants, opacifying agents, stabilizers, emollients, silicones, insect repellents, perfumes, preservatives, surfactants, fillers, pigments, polymers, propellants, alkalinizing or acidifying agents or any other ingredient customarily used in the cosmetic and/or dermatological field.

Of course, those skilled in this art will be careful to choose the possible additional compound(s) cited above and/or their quantities such that the advantageous properties intrinsically attached to the ultrafine emulsions in accordance with the invention are not, or not substantially, impaired by the addition(s) envisaged.

Among the organic solvents lower alcohols and polyols may be mentioned.

Among the thickeners, there may be mentioned crosslinked acrylic polymers such as the Carbomers provided by Noveon, acrylate/C10-30 alkyl acrylate crosslinked polymers of the Pemulen type provided by Noveon or polyacrylate-3 sold under the name Viscophobe DB 1000 by Amerchol); polymers derived from acrylamido-2-methyl-propanesulphonic acid (Hostacerin AMPS provided by Clariant, Sepigel 305 provided by Seppic), synthetic neutral polymers such as poly-N-vinylpyrrolidone, polysaccharides such as guar and xanthan gums, and modified or unmodified cellulose derivatives such as hydroxypropylated guar gum, methylhydroxyethylcellulose and hydroxypropylmethylcellulose.

The emulsions according to the invention find application in a large number of treatments, in particular cosmetic treatments, of the skin, the lips and the hair, including the scalp, in particular for the protection and/or care of the skin, the lips and/or the hair, and/or for making up the skin and/or the lips.

The present invention also features the use of the emulsions according to the invention as defined above for the manufacture of compositions for the cosmetic treatment of the skin, the lips and the hair, including the scalp, in particular for the protection and/or care of the skin, the lips and/or the hair, and/or for making up the skin and/or the lips.

The cosmetic compositions according to the invention may, for example, be used as care and/or sun protection product for the face and/or the body. They can also be packaged in the form of creams, milk, gel creams, or alternatively fluid lotions, in particular vaporizable fluid lotions (the compositions according to the invention indeed having the additional advantageous property of being easily dilutable with water).

The compositions according to the invention in the form of vaporizable fluid lotions in accordance with the invention are applied to the skin or the hair in the form of fine particles by means of pressurized devices. The devices in accordance with the invention are well known to persons skilled in the art and comprise nonaerosol pumps or "atomizers", the aerosol containers comprising a propellant and aerosol pumps using compressed air as propellant. The latter are described in U.S. Pat. Nos. 4,077,441 and 4,850,517.

The compositions packaged as an aerosol in accordance with the invention contain in general conventional propellants such as, for example, the hydrofluorinated compounds dichlorodifluoromethane, difluoroethane, dimethyl ether, isobutane, n-butane, propane, trichlorofluoromethane. They are preferably present in quantities ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The procedure which was followed for preparing the emulsion 1 was as follows: the fatty phase (A) and aqueous phase (B) were both heated beforehand to a temperature of the order of 90° C.; the phase (C) containing nanopigments was introduced into and dispersed in the fatty phase (A), with vigorous stirring of the latter by means of a MORITZ type turbine (1,000 rpm); and finally the aqueous phase (A) was added to the resulting dispersion, still with mechanical stirring. This latter emulsification step was performed at 80° C., that is to say at a temperature greater than the phase inversion temperature of the system, which is here 72° C. (PIT).

The following emulsion 1 was prepared (% by weight expressed relative to the whole formulation):

| | Constituents | Emulsion 1 (invention) |
|---|---|---|
| Phase A | Oxyethylenated stearyl alcohol (12 EO) (Emulgin B1 - Cognis) | 6.6 |
| | Glyceryl stearate (Tegin 90 - Goldschmidt) | 3.4 |
| | Liquid paraffin | 30 |
| | Polydimethylsiloxane (Dow Corning 200 Fluid - Dow Corning) | 0.5 |
| | Cetearyl alcohol/cetearyl glucoside (88/12) (Montanov 68 - Seppic) | 2.0 |
| | Ethylhexyl methoxycinnamate (Uvinul MC 80 - BASF) | 7.0 |
| | 1,1-Dicarboxy(2,2'-dimethylpropyl)-4,4-diphenylbutadiene | — |
| | Nanopigment titanium oxide $TiO_2$ (MT 100T - TAYCA) | 5.0 |
| Phase B | Glycerin | 5.0 |
| | Preservatives | qs |
| | Demineralized water | qs 100 |
| Phase C | Nanopigment titanium oxide $TiO_2$ (MT 100T - TAYCA) | 5.0 |

The emulsion 1 obtained is stable over time, has good stability to water and an efficacy level in UV-A similar to a composition of the same type containing 1,4-benzene[di(3-methylidene-10-camphorsulphonic)] acid and its different salts. Its cosmetic performance is comparable to that obtained with a conventional oil/water emulsion.

Comparative Study of the Stability to Water:

The following conventional oil/water emulsion 2 is prepared (% by weight expressed relative to the whole formulation):

| | Constituents | Emulsion 2 (outside invention) |
|---|---|---|
| Phase A | Mixture of glyceryl monostearate/polyethylene glycol stearate (100 EO) (Arlacel 165 - Uniquema) | 1.0 |
| | Cetyl alcohol (Lanette 16 - Cognis) | 0.5 |
| | Fatty acid of plant origin (Stearine TP - Stéarinerie Dubois) | 1.5 |
| | Polydimethylsiloxane (Dow Corning 200 Fluid - Dow Corning) | 0.5 |
| | Cetearyl alcohol/cetearyl glucoside (88/12) (Montanov 68 - Seppic) | 2.0 |
| | $C_{12}$-$C_{15}$ alcohol benzoate (Finsolv TN - WITCO) | 5 |
| | Ethylhexyl methoxycinnamate (Uvinul MC 80 - BASF) | 7 |
| | 1,1-Dicarboxy(2',2'-dimethylpropyl)-4,4-diphenylbutadiene | 5 |
| | Nanopigment titanium oxide $TiO_2$ (MT 100T - TAYCA) | 5 |
| Phase B | Glycerin | 5 |
| | Hexadecyl alcohol phosphate, potassium salt (Amphisol K - Roche Vitamins) | 1 |
| | Xanthan gum (Keltrol T - CP Kelco) | 0.2 |
| | Acrylates/$C_{10}$-$C_{30}$ alkyl acrylates (Permulen TR 1 - Noveon) | 0.1 |
| | Triethanolamine | qs |
| | Preservatives | qs |
| | Demineralized water | qs 100 |

Manufacturing Procedure:

The fatty phase (A) is weighed and heated on a water bath at 70° C. The aqueous phase (B) is weighed in the final beaker and heated on a water bath at 70° C. The phase (A) is introduced into the aqueous phase (B) with rotor type (Moritz) stirring. The medium is allowed to cool to room temperature, it is neutralized and packaged.

The following oil/water emulsion 3 is then prepared containing the UV-A-screening agent: 1,4-benzene[di(3-methylidene-10-camphorsulphonic)] acid according to the phase inversion technique under the same conditions as Example 1 (% by weight expressed relative to the whole formulation):

| | Constituents | Emulsion 3 (outside invention) |
|---|---|---|
| Phase A | Oxyethylenated stearyl alcohol (12 EO) (Emulgin B1 - Cognis) | 6.6 |
| | Glyceryl stearate (Tegin 90 - Goldschmidt) | 3.4 |
| | Liquid paraffin | 30 |
| | Polydimethylsiloxane (Dow Corning 200 Fluid - Dow Corning) | 0.5 |
| | Cetearyl alcohol/cetearyl glucoside (88/12) (Montanov 68 - Seppic) | 2.0 |
| | Ethylhexyl methoxycinnamate (Uvinul MC 80 - BASF) | 7.0 |
| | 1,1-Dicarboxy(2',2'-dimethylpropyl)-4,4-diphenylbutadiene | — |
| | Nanopigment titanium oxide $TiO_2$ (MT 100T - TAYCA) | 5.0 |
| Phase B | Glycerin | 5.0 |
| | 1,4-Benzene[di(3-methylidene-10-camphorsulphonic)] acid (Mexoryl SX - Chimex) | 5.0 |
| | Preservatives | qs |
| | Demineralized water | qs 100 |

-continued

| Constituents | | Emulsion 3 (outside invention) |
|---|---|---|
| Phase C | Nanopigment titanium oxide TiO$_2$ (MT 100T - TAYCA) | 5.0 |

The stability to water of the sun protection factor (SPF) of the emulsions 1, 2 and 3 as defined above was measured and compared according to the following protocol:

| | |
|---|---|
| Spreading support: | plates of the Transpore ® type mounted in a slide frame |
| Quantity deposited: | 30 mg |
| Application: | with the bare finger on both sides of the plate |
| Quantity per application: | 19 mg ± 0.5 (that is 0.75 mg/cm$^2$) |
| Number of samples: | 4 measurements per application and 5 applications per formula |
| Bath: | immersion and stirring of the samples in a water bath at 30° C. for 10 min |

Determination of the SPFs before and after bathing:

| | |
|---|---|
| Measuring apparatus: | spectroradiometer SPF-290 (Optometrics) recording of the monochromatic sun protection factors every 5 nm between 290 and 400 nm |
| Mode of calculation of the SPFs: | method described by B. L. Diffey et al in J. Soc. Cosmet. 40-127-133 (1989) |
| Source spectrum: | Diffey sun |
| Activity spectrum: | erythema CIE 1987 |

The percentage of residual efficacy is then calculated after bathing according to the following equation: % residual efficacy=100×(average SPF after bathing—1)/average SPF after bathing−1

The results obtained on the emulsions 1, 2, and 3 are as follows:

| Composition | % residual efficacy after bathing |
|---|---|
| Emulsion 1 (invention) | 68% |
| Emulsion 2 (outside invention) | 51% |
| Emulsion 3 (outside invention) | 27% |

It is observed that the emulsion 1 obtained according to the phase inversion technique containing as UV-A-screening agent a compound 4,4-diarylbutadiene has a stability to water 2.5 times higher than the emulsion 3 obtained according to the phase inversion technique containing nanopigments of TiO2 and as UV-A-screening agent of equivalent efficacy: 1,4-benzene[di(3-methylidene-10-camphorsulphonic)] acid.

It is observed that the emulsion 1 obtained according to the phase inversion technique containing nanopigments of TiO2 and as UV-A-screening agent a compound 4,4-diarylbutadiene has a better stability to water compared with the emulsion 2 of the conventional oil/water type containing the same screening system.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable UV-photoprotective, phase inverted oil-in-water emulsion, the average size of the globules which constitute the oily phase thereof ranging from 100 nm to 1,000 nm, comprising inorganic metal oxide nanopigments and at least one organic UV-screening agent, and also comprising at least one organic 4,4-diarylbutadiene UV-A-screening agent.

2. The oil-in-water emulsion as defined by claim 1, the average size of the oily globules ranging from 100 to 500 nm.

3. The oil-in-water emulsion as defined by claim 1, at least 90% in numerical terms of said globules having a size ranging from 100 nm to 1,000 nm.

4. The oil-in-water emulsion as defined by claim 1, comprising nanopigments of titanium, zinc, iron, zirconium or cerium oxides, or mixtures thereof, whether coated or uncoated.

5. The oil-in-water emulsion as defined by claim 4, comprising nanopigments of titanium oxide, whether coated or uncoated.

6. The oil-in-water emulsion as defined by claim 5, comprising nanopigments of titanium oxide in rutile, anatase or amorphous form.

7. The oil-in-water emulsion as defined by claim 1, the content by weight of the nanopigments ranging from 0.5% to 40% of the total weight of the composition.

8. The oil-in-water emulsion as defined by claim 1, said at least on 4,4-diarylbutadiene UV-A-screening agent having the following formula (I):

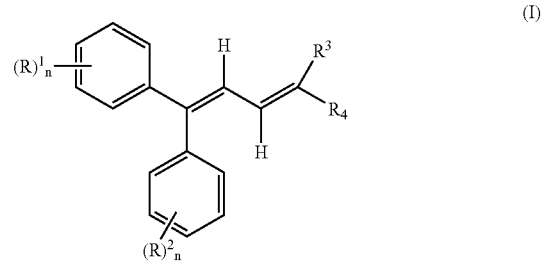

in which the diene system is of the Z,Z; Z,E; E,Z or E,E configuration or mixture of said configurations, and wherein:

$R^1$ and $R^2$, which may be identical or different, are each hydrogen, a $C_1$-$C_{20}$ alkyl radical, a $C_2$-$C_{10}$ alkenyl radical, a $C_1$-$C_{12}$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulfonate residue or an ammonium residue;

R³ is a group COOR⁵, COR⁵, CONR⁵R⁶, CN, O=S(—R⁵)=O, O=S(—OR⁵)=O, R⁷O—P—(—OR⁸)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl;

R⁴ is a group COOR⁶; COR⁶; CONR⁵R⁶; CN; O=S(—R⁶)=O; O=S(—OR⁶)=O;

R⁷O—P—(—OR⁸)=O; a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl; an optionally substituted $C_3$-$C_7$ heteroaryl radical;

the radicals R⁵ to R⁸, which may be identical or different, are each hydrogen, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ bicycloalkenyl radical, a $C_7$-$C_{10}$ cycloalkenyl radical, an optionally substituted aryl radical, an optionally substituted heteroaryl radical; n ranges from 1 to 3; with the proviso that the radicals R³ to R⁸ can together form, with the carbon atoms from which they depend, a $C_5$-$C_6$ ring which may be fused.

9. The oil-in-water emulsion as defined by claim 8, wherein said at least one compound of formula (I):

n=1 or 2;

R¹ and R², which may be identical or different, are each hydrogen, a $C_1$-$C_{20}$ alkyl radical, a $C_1$-$C_{12}$ alkoxy radical, a $C_1$-$C_{12}$ monoalkylamino radical, a $C_1$-$C_{12}$ dialkylamino radical, a water-solubilizing substituent selected from among a carboxylate group, a sulfonate group or an ammonium residue;

R³ is a group COOR⁵, COR⁵, CONR⁵R⁶, a $C_1$-$C_{20}$ alkyl radical, a $C_3$-$C_{10}$ cycloal radical, a $C_3$-$C_{10}$ cycloalkenyl radical, a $C_7$-$C_{10}$ bicycloalkyl radical, optionally substituted phenyl, naphthyl or thienyl;

R⁴ is a group COOR⁶, COR⁶, CONR⁵R⁶, a $C_1$-$C_{20}$ alkyl radical, a $C_3$-$C_6$ cycloalk radical, a $C_3$-$C_{10}$ cycloalkenyl radical, a $C_7$-$C_{10}$ bicycloalkyl radical, optionally substituted phenyl, naphthyl or thienyl; and the radicals R⁵ and R⁶, which may be identical or different, are each hydrogen, a $C_1$-$C_{12}$ alkyl radical, a $C_3$-$C_{10}$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

10. The oil-in-water emulsion as defined by claim 9, wherein said at least one compound of formula (I):

R¹ and R², which may be identical or different, are each hydrogen, a $C_1$-$C_{20}$ alkyl radical, a $C_1$-$C_{20}$ alkoxy radical, a water-solubilizing substituent selected from among a carboxylate group, a sulfonate group or an ammonium residue;

R³ is a group COOR⁵, COR⁵, CONR⁵R⁶;

R⁴ is a group COOR⁶, COR⁶, CONR⁵R⁶; and the radicals R⁵ and R⁶, which may be identical or different, are each hydrogen, a $C_1$-$C_{12}$ alkyl radical, a $C_3$-$C_6$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

11. The oil-in-water emulsion as defined by claim 10, said at least one compound of formula (I) having the following formula (I'):

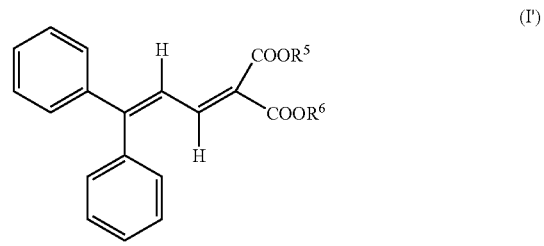

(I')

wherein the radicals R⁵ and R⁶, which may be identical or different, are each hydrogen, a $C_1$-$C_{20}$ alkyl radical, a $C_3$-$C_6$ cycloalkyl radical, a $C_3$-$C_{10}$ cycloalkenyl radical.

12. The oil-in-water emulsion as defined by claim 11, said compound of formula (I') comprising the 1,1-dicarboxy(2'2'-dimethylpropyl)-4,4-diphenylbutadiene derivative having the structure:

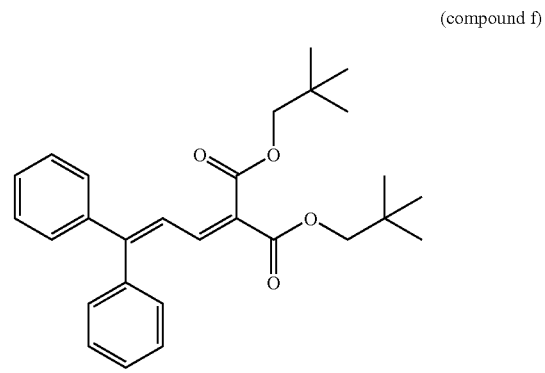

(compound f)

13. The oil-in-water emulsion as defined by claim 1, said at least one 4,4-diarylbutadiene UV-A-screening agent having the following formula (II):

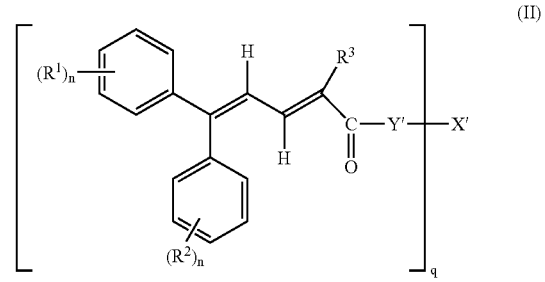

(II)

in which the diene system is of the Z,Z; Z,E; E,Z or E,E configuration or mixture of said configurations and wherein:

R¹, R², R³ and n have the meanings indicated in the formula (I);

Y' is a group —O— or —NR⁹—;

R⁹ is hydrogen, a linear or branched $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an aryl radical, a heteroaryl radical;

X' is a residue of a linear or branched, aliphatic or cycloaliphatic $C_2$-$C_{20}$ polyol comprising from 2 to 10 hydroxyl groups and having the valency q; with the proviso that the carbon chain of said residue may be interrupted by one or more sulfur or oxygen atoms, one or more imine groups, one or more $C_1$-$C_4$ alkylimino groups; and q ranges from 2 to 10.

14. The oil-in-water emulsion as defined by claim 13, wherein said compound of formula (II):

$R^1$ and $R^2$, which may be identical or different, are each hydrogen, a $C_1$-$C_{12}$ alkyl radical, a $C_1$-$C_8$ alkoxy radical, a water-solubilizing substituent selected from among a carboxylate group, a sulfonate group or an ammonium residue;

$R^3$ is a group $COOR^5$, $CONR^5R^6$, CN; a $C_3$-$C_{10}$ cycloalkyl radical, a $C_7$-$C_{10}$ bicycloalkyl radical;

$R^5$ and $R^6$, which may be identical or different, are each a linear or branched $C_1$-$C_{20}$ alkyl radical, a $C_3$-$C_{10}$ cycloalkyl radical, a $C_7$-$C_{10}$ bicycloalkyl radical, optionally substituted naphthyl or phenyl; and X' is a $C_2$-$C_{20}$ polyol residue comprising from 2 to 6 hydroxyl groups.

15. The oil-in-water emulsion as defined by claim 14, wherein said compound of formula (II), X' is an ethanol or pentaerythritol residue.

16. The oil-in-water emulsion as defined by claim 15, said compound of formula (II) being selected from among:

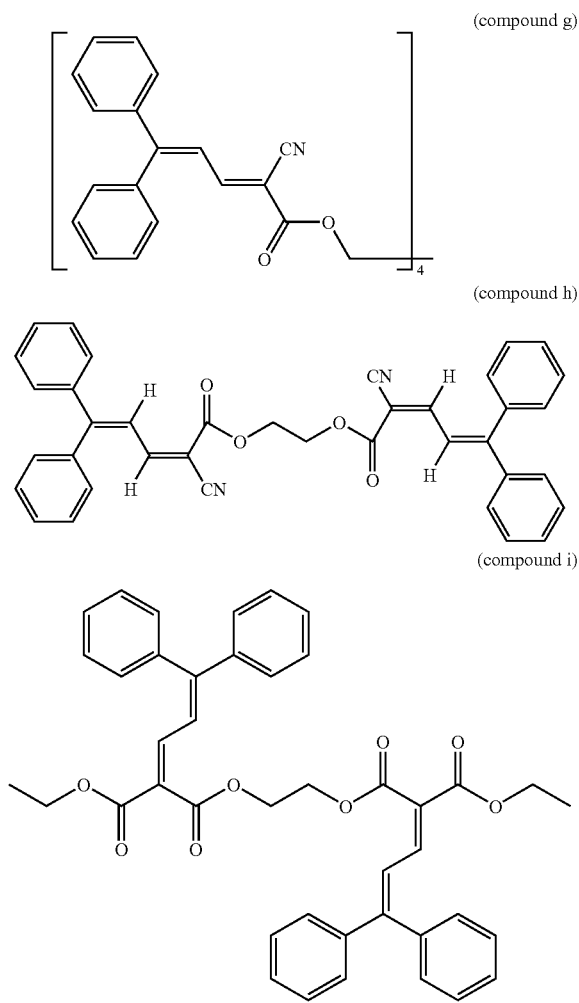

(compound g)

(compound h)

(compound i)

17. The oil-in-water emulsion as defined by claim 1, said at least one 4,4-diarylbutadiene UV-A screening agent constituting from 0.1% to 20% by weight relative to the total weight of the emulsion.

18. The oil-in-water emulsion as defined by claim 1, further comprising at least one additional organic sunscreening agent active in the UV-A and/or UV-B regions, water-soluble, fat-soluble or insoluble in the usual cosmetic solvents.

19. The oil-in-water emulsion as defined by claim 18, comprising at least one additional organic screening agent selected from among the anthranilates; cinnamic derivatives; dibenzoylmethane derivatives; salicylic derivatives, camphor derivatives; triazine derivatives; benzophenone derivatives; β,β'-diphenyl acrylate derivatives; benzotriazole derivatives; benzalmalonate derivatives; benzimidazole derivatives; imidazolines; bis-benzoazolyl derivatives; p-aminobenzoic acid (PABA) derivatives; benzoxazole derivatives;

methylenebis(hydroxyphenylbenzotriazole) derivatives; screening polymers and screening silicones; dimers derived from α-alkylstyrene and mixtures thereof.

20. The oil-in-water emulsion as defined by claim 19, comprising at least one additional organic screening agent selected from among:

Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic acid,
Disodium Phenyl Dibenzimidazole Tetra-sulfonate,
2,4,6-Tris(4'-diisobutyl aminobenzalmalonate)S-triazine
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl) imino-1,3,5-triazine,
and mixtures thereof.

21. The oil-in-water emulsion as defined by claim 1, further comprising at least one agent for artificial bronzing and/or tanning of the skin.

22. The oil-in-water emulsion as defined by claim 1, further comprising at least one cosmetic adjuvant selected from among organic solvents, ionic or nonionic thickeners, demulcents, humectants, opacifying agents, stabilizers, emollients, silicones, insect repellents, perfumes, preservatives, surfactants, fillers, pigments, polymers, propellants, alkalinizing or acidifying agents or any other ingredient commonly employed in the cosmetic and/or dermatological field.

23. The oil-in-water emulsion as defined by claim 1, comprising an emulsifying system.

24. The oil-in-water emulsion as defined by claim 23, said emulsifying system comprising one or more emulsifying agents of the nonionic type and selected from among polyoxyethylenated and/or polyoxypropylenated fatty alcohols, and optionally polyoxyethylenated and/or polyoxypropylenated fatty acid esters and polyol esters.

25. The oil-in-water emulsion as defined by claim 24, said emulsifying system having an overall HLB ranging from about 9.5 to 11.5.

26. The oil-in-water emulsion as defined by claim 25, said emulsifying agent constituting from 0.5% to 40% by weight relative to the total weight of the emulsion.

27. The oil-in-water emulsion as defined by claim 1, the aqueous phase thereof constituting from 50% to 95% of the total weight of the emulsion.

28. The oil-in-water emulsion as defined by claim 1, the oily phase thereof constituting from 5 to 50% of the total weight of the composition.

29. A method for formulating an oil-in-water emulsion as defined by claim 1, comprising:
  (i) mixing a fatty phase and an aqueous phase in the presence of an emulsifying system and of at least one 4,4-diarylbutadiene UV-A-screening agent, with stirring, said mixing being carried out at a temperature greater than the phase inversion temperature (PIT) of the medium, so as to obtain a water-in-oil type emulsion.
  (ii) adjusting the temperature of the emulsion thus obtained to a temperature below said phase inversion temperature, thereby obtaining an ultrafine emulsion of the oil-in-water type; and
  (iii) introducing inorganic nanopigments during the step (i) and/or at the end of step (ii).

30. A method for photoprotecting the skin, lips and/or hair against the damaging effect of UV-radiation, comprising topically applying thereon, a thus effective amount of a stable UV-photoprotective, phase inverted oil-in-water emulsion, the average size of the globules which constitute the oily phase thereof ranging from 100 nm to 1,000 nm, comprising inorganic metal oxide nanopigments and at least one organic UV-screening agent, and also comprising at least one organic 4,4-diarylbutadiene UV-A-screening agent.

* * * * *